(12) United States Patent
Donnet et al.

(10) Patent No.: US 9,888,979 B2
(45) Date of Patent: Feb. 13, 2018

(54) METHOD OF POWDER BLASTING FOR CLEANING OF TOOTH SURFACES

(71) Applicant: Ferton Holding S.A., Delemont (CH)

(72) Inventors: Marcel Donnet, Saint Jean de Gonville (FR); Joerg Wittmann, Darmstadt (DE)

(73) Assignee: FERTON HOLDING S.A. (CH)

( * ) Notice: Subject to any disclaimer, the term of this patent is extended or adjusted under 35 U.S.C. 154(b) by 168 days.

(21) Appl. No.: 13/927,257

(22) Filed: Jun. 26, 2013

(65) Prior Publication Data

US 2013/0337413 A1 Dec. 19, 2013

Related U.S. Application Data

(62) Division of application No. 12/722,296, filed on Mar. 11, 2010, now abandoned.

(30) Foreign Application Priority Data

Mar. 12, 2009 (EP) ..................................... 09155004

(51) Int. Cl.
| | | |
|---|---|---|
| *A61C 3/025* | (2006.01) | |
| *A61Q 11/00* | (2006.01) | |
| *A61K 8/02* | (2006.01) | |
| *A61K 8/19* | (2006.01) | |
| *A61K 8/34* | (2006.01) | |
| *B24C 7/00* | (2006.01) | |
| *B24C 11/00* | (2006.01) | |

(52) U.S. Cl.
CPC .............. *A61C 3/025* (2013.01); *A61K 8/022* (2013.01); *A61K 8/19* (2013.01); *A61K 8/345* (2013.01); *A61Q 11/00* (2013.01); *B24C 7/0046* (2013.01); *B24C 11/005* (2013.01)

(58) Field of Classification Search
USPC ............................. 424/49; 433/88, 215, 216
See application file for complete search history.

(56) References Cited

U.S. PATENT DOCUMENTS

| | | | |
|---|---|---|---|
| 3,341,415 A | 9/1967 | Scott | |
| 3,882,638 A | 5/1975 | Black | |
| 4,174,571 A | 11/1979 | Gallant | |
| 5,462,760 A | 10/1995 | Serpelloni et al. | |
| 5,810,587 A | 9/1998 | Bruns et al. | |
| 6,126,444 A | 10/2000 | Horiguchi | |
| 6,165,511 A | 12/2000 | Schwarz et al. | |
| 6,485,304 B2 | 11/2002 | Beerstecher et al. | |
| 6,648,644 B1 | 11/2003 | Flemmig et al. | |
| 2002/0004188 A1 | 1/2002 | Beerstecher et al. | |
| 2006/0275223 A1* | 12/2006 | Burr ....................... | A61Q 11/00 424/49 |

FOREIGN PATENT DOCUMENTS

| | | | |
|---|---|---|---|
| DE | 198 04 065 | | 12/1999 |
| DE | 100 26 718 | | 12/2001 |
| EP | 0 630 573 | | 12/1994 |
| EP | 1 159 929 | | 12/2001 |
| EP | 1 374 871 | | 1/2004 |
| EP | 1 972 675 | | 3/2008 |
| EP | 1 905 430 | | 4/2008 |
| JP | 10-306048 | | 11/1998 |
| JP | 11-192244 | * | 7/1999 |
| JP | 11-244303 | * | 9/1999 |
| JP | 2000-204354 | | 7/2000 |
| WO | WO 97/04741 | | 2/1997 |
| WO | 9840434 | | 9/1998 |
| WO | 00/53154 | | 9/2000 |

OTHER PUBLICATIONS

Notice of Opposition to a European Patent in parallel European Patent No. EP2228175 dated Mar. 20, 2014.
Performance comparison of a Glycine based and an Erythritol based air polishing powder, Comparative Examples cited in Notice of Opposition dated Mar. 20, 2014.

* cited by examiner

*Primary Examiner* — Lezah Roberts
(74) *Attorney, Agent, or Firm* — Ostrolenk Faber LLP

(57) ABSTRACT

A method for cleaning tooth surfaces with a powder and a powder mixture, preferably by powder blasting with a powder-jet device, said device mixing the powder or the powder mixture with air to form a powder/air mixture, wherein said powder and/or powder mixture is an alditol or contains such alditol. Preferably, mannitol and/or erythritol are used, because of their anti-cariogenic effect. Xylitol is also suitable for cleaning tooth surfaces, especially of less strongly mineralized tooth surfaces like dentine.

19 Claims, 1 Drawing Sheet

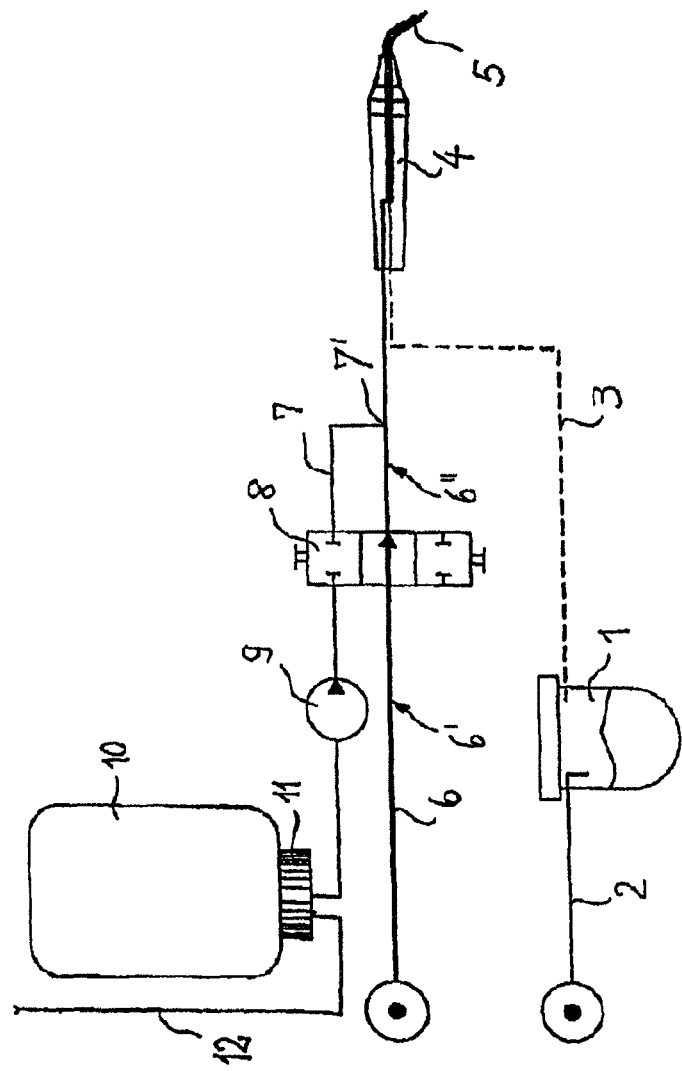

METHOD OF POWDER BLASTING FOR CLEANING OF TOOTH SURFACES

CROSS-REFERENCE TO RELATED APPLICATION

This is a divisional application of U.S. application Ser. No. 12/722,296, filed Mar. 11, 2010, claiming priority to EP 09 155 004.6, filed Mar. 12, 2009, both incorporated by reference in their entireties.

BACKGROUND

Field

The disclosure relates to a powder for powder blasting with a powder-jet device or a powder mixture for powder blasting with a powder-jet device as described, for example, in EP 1 159 929. Furthermore, the disclosure relates to the use of such a powder and powder mixture, respectively, for the preparation of an agent or material for the powder-jet treatment, especially the powder-jet cleaning of tooth surfaces, preferably tooth root surfaces and dentine.

Related Art

FIG. 1 shows a dental abrasive spraying device disclosed in EP 1 159 929, incorporated by reference. It can be used not only with conventional tap water from a water supply (12), but also with other fluids. A dental abrasive spraying device has a hand-piece (4) nozzle for spraying a dental powder contained in a reservoir (1), together with a carrier gas and a fluid aiding mixing of the powder with the carrier. There are two separate pressure feeds (3,6). Pressurized air comes from the feed (6). A feed (2) supplies pressurized air to swirl the powder in reservoir (1). The swirled powder is led through line (3) to the nozzle (4), where additional air arrives through line (6') and liquid through line (7). In the device: (a) there is an exchangeably-fixed separate container (10) storing a rinsing liquid which can be supplied separately or together with the water, powder and carrier gas to the nozzle; (b) a branch-line (7) is connectable via a valve (8) to container (10) to allow the liquid to be fed to the nozzle; and (c) there is a suction pump (9) upstream of the valve (8). This device can supply either liquid from line (7), or air from line (6'), to be mixed with the air/powder mixture from line (3).

Also of background interest, disclosing relevant methods and equipment, are U.S. application Ser. No. 11/956,596 filed Dec. 14, 2007, now U.S. Pat. No. 7,762,812, Issued Jul. 27, 2010, and U.S. application Ser. No. 12/047,869 filed Mar. 13, 2008, now U.S. Pat. No. 7,980,923, Issued Jul. 19, 2011, both incorporated by reference.

Powders of background interest are already known from U.S. Pat. No. 3,882,638 or U.S. Pat. No. 4,174,571, whereas the further development of the second mentioned document aims at the provision of particularly gentle powders like glutamate or sodium gluconate being less abrasive in comparison to the hitherto known powders of sodium bicarbonate or Iceland spar, and hence will, to a lesser extent, adversely affect sensitive surfaces, like e.g. tooth root surfaces, but also dental enamel surfaces. Preferred grain sizes range from 140 µm to 200 µm, in case of stronger abrasively affecting powders they also range from 20 µm to 70 µm.

When treating sensitive tooth surfaces, like root dentine or others less strongly mineralized tooth surfaces, with a powder-jet device, it is recommended using powders with a density of no more than 2.0 g/cm$^3$ and a mean grain size of no more than 45 µm. WO 00/53154 discloses such particularly gentle powders for the cleaning of subgingival tooth surfaces, like e.g. root dentine. U.S. Pat. No. 6,126,444 discloses the same, wherein sensitive, in particular subgingival tooth root surfaces were treated with a powder consisting of e.g. crystalline cellulose with a mean grain size of 6, 15, 20, 50 or also 120 µm; and the cleaning efficiency is similarly good as the one obtained when using a powder consisting of sodium bicarbonate, whereas the abrasion of root dentine is considerably less. Whereas U.S. Pat. No. 6,126,444 discloses water insoluble agents, WO 00/53154 discloses water soluble agents like amino acids, sugar or organic acids and the salts thereof, which have the advantage that the powder dissolves in water upon application to the tooth and particularly does not gather in the gingival pockets, where water insoluble agents cause an unpleasant feeling and might possibly even lead to an infection of the gingival pocket or the gingiva. These powders, however, have the disadvantage that, due to one or several grinding and sieving steps, the preparation or manufacturing thereof is expensive and laborious.

Whereas powders consisting of smaller particles have a lower impulse when hitting the tooth surface, and hence abrade less material, the same applies to lighter agents or materials which also have a lower impulse and therefore abrade less material. From U.S. Pat. No. 6,126,444, however, it is evident that powders with a smaller mean grain size obtain similarly good cleaning effects as do powders with larger mean grain sizes. Therefore, neither grain size nor density alone, give information about the powder—in case of an almost similarly good cleaning efficiency—having a stronger or weaker abrasive effect on the tooth surface.

U.S. Pat. No. 5,810,587 discloses another composition for cleaning sensitive tooth surfaces by means of powder-jet devices, wherein, on the one hand, a good cleaning result for the removal of tooth deposit/dental plaque is to be obtained, and, at the same time, an abrasiveness as slight as possible is to be obtained when impinging upon sensitive tooth surfaces. U.S. Pat. No. 5,810,587 recommends using very finely particled materials which are put together to larger "snowballs" and burst upon hitting the tooth surface. Particles ranging in size from 0.01 to 5 µm are formed to larger spheres having dimensions from 10 to 200 µm and breaking apart when they impinge upon the tooth surface. Gibbsite is recommended as raw material.

Substantially, five factors are decisive for the abrasiveness of a powder used for powder blasting. Apart from particle speed, hardness and crushing resistance of the particles, the surface condition and the mass are also decisive. In case of equal mass, large particles with a lower density have almost the same abrasiveness as smaller particles with a higher density. Smaller particles, however, can be used or processed suboptimal in the known powder-jet devices. Generally, such a powder is present in a powder chamber as is shown in EP 1 159 929. Air is blown into said powder chamber, to disperse the powder, wherein the resulting air/powder mixture is fed to a nozzle, to which also water is supplied in general by a separate supply line. At the nozzle end, the air/powder mixture, surrounded by a water jet, exits and impinges upon the tooth surface which is generally arranged at a distance of 1 mm and 5 mm from the nozzle outlet.

From U.S. Pat. No. 4,174,571, it is known to use water-soluble powders that are considered by humans as not having an unpleasant taste. Agglutination inside the powder chamber should also be avoided, why the powder should also not be hygroscopic. This property can also be improved by adding further finely particled substances, like pyrogenic silica.

Further criteria for the selection of suitable jet means are mixing and flight characteristics of the used particles. Upon swirling in the powder chamber, care has to be taken that a constant loading of the outgoing airstream takes place, independent of the amount of powder filled into the powder chamber. This can only be ensured when the powder is uniformly stirred by the airstream and when the pourability, for example, is restricted by the formation of densified areas. Smaller particles tend more to form such densified area than larger particles which, due to their mostly larger mass, are often less suitable for being stirred by the airstream. In addition, the miscibility depends on the agent used. At the same time, it should be possible that the powder be processed by the used powder-jet devices, and the preparation or manufacturing of the powder should be as cost-efficient as possible.

Furthermore, a powder for powder blasting should have a corrosion tendency as low as possible and wear out the jet nozzle as little as possible. It should be possible to manufacture the powder, in the preferred size, preferably directly and without requiring further milling processes and the powder should be eudermic. The powder should be well tolerated by humans and, if possible, have an acceptable taste. In order to shorten or avoid costly and time-consuming applications procedures, the powder should preferably have few side effects and a good digestibility.

SUMMARY

Therefore, it would be desirable to avoid the aforesaid disadvantages of conventional powders and, at the same time, meet the aforesaid requirements and demands as extensively as possible.

Highly advantageous for these goals are the powders and powder mixtures disclosed and claimed herein. Moreover, a powder blasting device, containing these powders and powder mixtures, is disclosed and claimed. Other embodiments are disclosed and claimed as well.

The inventors have surprisingly found that almost all afore-said requirements to such a powder can be met, when an alditol is used as powder. Altidols are acyclic polyols having the formula $HOCH_2[CH(OH)]_nCH_2OH$, which structurally derive from carbohydrates. They are also called sugar alcohols.

Sugar alcohols, which are especially preferred in the present application, are mannitol, erythritol, xylitol, sorbitol or threitol. Alditols have a sweet taste, are not cariogenic and show a laxative effect only after the consumption of more than 20 to 30 g/day, that is to say, they can, just like that, be used for powder-jet cleaning of tooth surfaces. Since alditols are used as sugar substitutes in dietetic food, they do not increase the blood glucose level and require no insulin to be metabolized. Hence, they are also suitable for diabetics and can, just like that, be used for powder-jet application.

Mannitol and erythritol turned out to be especially preferred alditols.

Mannitol is an alditol with four CH(OH) groups and is used as a sugar substitute (E 421), as well as a pharmaceutical drug in the production of tablets. It is uncoloured, a sweet tasting crystal and has a density of approx. $1.52\ g/cm^3$. Due to its easy solubility in water, since, after impinging on the tooth surface, it can be dissolved and rinsed out. The molar mass of mannitol is 182.17 g/mol. The molecular formula is $C_6H_{14}O_6$. Mannitol is available on the market as the trademarks Osmofundin®, Osmosteril® or also Bronchitol®.

Contrary to the hitherto known kinds of powder, like glycine, sodium gluconate or sodium hydrogen carbonate, mannitol has many advantages. In comparison to glycine, mannitol wears off the jet nozzle less; but shows, in comparison to glycine, a comparable abrasiveness in case of a similar particle size. Furthermore, mannitol cleans the tooth surface better than glycine, without adversely affecting the sensitive dentine. Simultaneously, it turned out that mannitol can be very well mixed with air in the powder receptacle, and that a uniform swirl takes place. Despite the small size of the particles, it raises less dust than, for example, glycine and thus can be better agitated and fed more uniformly to the nozzle of the powder-blasting device. This improves the evenness of the tooth treatment.

Furthermore, mannitol can be prepared as powder directly in the desired sizes and needs not, like, e.g., sodium hydrocarbonate or glycine, be grinded and sieved to the desired size. In addition, the tolerance of mannitol is significantly better. Glycine is cytotoxic and may, upon skin contact, cause irritations. Mannitol is a sugar substitute and can be used as food. It is water-soluble, does not clot and has a sweet taste.

The preferred mean grain size of the powder should be no larger than 45 µm, preferably no larger than 35 µm, more preferred approximately between 10 µm and approx. 30 µm. A suitable mean grain size of mannitol powder for cleaning sensitive tooth surfaces is about 20 µm to 30 µm.

The powder has a density of not more than $2.0\ g/m^3$, preferably no more than $1.8\ g/m^3$, and more preferred no more than $1.55\ g/cm^3$. Much preferred densities range between $1.4\ g/m^3$ and $1.5\ g/m^3$. Furthermore, a special embodiment of the powder has a Mohs hardness of no more than 5, preferably no more than 3.5, much preferred no more than 2.5. Furthermore, the powder has a molar mass of no less than 90 g/mol, preferably no less than 110 g/mol, much preferred no less than 120 g/mol. Long-chain hydrocarbons thereby form particles of a lower density, i.e. with a larger contact surface at equal mass, leading to improved swirl properties in the swirl chamber.

While glycine, with a particle size of less than 20 µm in the powder chamber of customary devices, can no longer be reliably swirled, and forms densified areas, even if materials for the increase of pourability, like pyrogenic silica, are added, and hence does not allow the airstream to be sufficiently enriched with the blasting material, this does not appear when using a powder made, for example, of erythritol.

Erythritol has two CH(OH) groups and is equally used a sugar substitute (E 968). It is solid at room temperature, has a density of $1.45\ g/cm^3$ and is water-soluble. Like mannitol, erythritol has the aforesaid positive properties and has, in comparison to other alditols like sorbitol, maltitol, lactite and isomalt, the advantage of a very high digestive tolerance. The abrasion measurements have surprisingly shown that, despite the somewhat lower density vis-à-vis mannitol, the abrasiveness of erythritol at equal size of the particles has slightly increased. The reason for this is probably the different crystal morphology of erythritol, leading to the formation of a sharp-edged surface of the particles. Erythritol is very advantageous because, in the mixing chambers of conventional powder-jet devices, it can reliably be swirled to low particle sizes of app. 12 µm. Although the effectiveness during the cleaning of tooth surfaces is similarly good as in larger mannitol or glycine powders, there is significantly less abrasiveness than with a powder containing glycine with a mean grain size of 20 μm, or mannitol with a mean grain size of 23 μm. Hence, erythritol is especially gentle to dentine.

Furthermore, a powder containing xylitol is suitable; an uncoloured, sweet tasting crystal with a molar mass of 152.15 g/mol and a low density of 0.77 g/cm$^3$. It can easily be dissolved in water and has the advantage of developing an anti-cariogenic effect. It is a natural sugar alcohol present in many sorts of vegetables and fruits (among others in plums, strawberries or raspberries). While metabolizing carbohydrates, xylitol is produced every day in the human body in the liver and has, because of its sweetish property, only positive characteristics of a dietary supplement. Xylitol is also suitable for diabetics.

Another suitable alditol is sorbitol with a density of 1.49 g/cm$^3$ and a molar mass of approximately 182.2 g/mol. Sorbitol forms uncoloured, odourless and hygroscopic needles having a sweet taste, and can be made from corn or wheat starch. It can easily be dissolved in water and therefore, because of its aforesaid properties, is especially suitable for the powder.

The disclosure also relates to a powder mixture for powder blasting with a powder-jet device, wherein the powder mixture contains at least two of the aforementioned powders, wherein each of the powders is present in a mass fraction (percentage) of no less than 2%, preferably no less than 10%, much preferred no less than 20%, based on the overall mass (total volume) of the aforesaid powders. Hence, the quantities only relate to the abrasively acting powders, wherein further components can, of course, be added to the powder mixture. A suitable agent for powder-jet cleaning of tooth surfaces therefore consists of the powder or the powder mixture described and taught herein, plus further components as necessary, like, e.g., finely particled silica gel, bleaching agents, analgetics, bacteriocides or flavour additives, which are added to the agent. Furthermore, air and water can be added to the agent, in order to be able to apply it, by means of the powder-jet device, onto the tooth surfaces to be treated.

Therefore, the disclosure also relates to a respective use of the powder or powder mixture for the preparation of an agent for powder-jet treatment, preferably cleaning, of tooth surfaces, preferably dentine.

The powder mixture additionally contains at least two of the aforesaid abrasive powders with a particle fraction (i.e. amount of substance) of no less than 5%, preferably no less than 10%, much preferred no less than 20%, based on the total number of particles (i.e. overall amount of substance) of the powders according to the aforesaid preferred embodiments. A much preferred powder mixture contains mannitol with a mass fraction (percentage) of about 30% and erythritol with a mass fraction (percentage) of about 70%. This corresponds to an amount-of-substance ratio (i.e. particle ratio) of about 1:6.

It has also surprisingly been found possible to add to a very fine and light powder, like e.g. erythritol, having a mean grain size of 12 μm, fractions of another powder having a bit larger particles, like e.g. mannitol with a mean grain size of approximately 20 μm. Due to the deposition of the larger particles, the airstream in the powder chamber can more easily stir the powder; and the risk of getting more compact, i.e. the formation of densified areas within the powder chamber, will be minimized, i.e. the swirling of the used powder mixture is still good, whereas, at the same time, a particularly finely particled powder impinges on the tooth surface, wherein the sensitive tooth root surfaces, in particular, are treated with care. In doing so, the abrasiveness of the powder mixtures increases only insignificantly, because the fraction of the added larger particles is not that high, and the powder with the larger particles, due to the morphology of the particle surface, has a less abrasive effect.

Whereas, in the prior art, further finely particled agents, like e.g. silica gel, were added to an abrasively acting (primary) powder to improve pourability, it has been realized by the inventors that the demands regarding the ability of swirling in the powder-jet device and the abrasiveness at the tooth surface can be met by a powder mixture which, in equal measure, meets the two competing requirements, that is to say the ability to swirl and the abrasiveness.

Hence, the disclosure also relates to a powder-jet device with a swirl chamber in which is present the powder or a powder mixture described and taught herein, and which is acted upon by an airstream such that the powder or powder mixture is swirled and, together with the airstream, can be fed to a nozzle.

Other features and advantages will become apparent from the following description of embodiments, with reference to the accompanying drawing.

BRIEF DESCRIPTION OF THE DRAWING

FIG. 1 shows a prior art dental abrasive spraying device suitable for use with the powders and powder mixtures and methods described herein.

DETAILED DESCRIPTION OF EXAMPLES

The powder or the powder mixture prepared as described herein was compared to a conventional powder from very fine sodium bicarbonate. At present, sodium bicarbonate with a mean grain size of about 65 μm is the most widespread powder for cleaning tooth surfaces, particularly dentine. Due to its considerably higher abrasiveness with regard to sensitive tooth surfaces, like, for example, at the neck of tooth, this powder is generally not used there. However, such a sodium bicarbonate powder, up to a powder size with a mean grain size of 10 μm, can still be processed in a commercially available powder-jet device. The abrasiveness with such smaller particles, however, is still identifiably higher than with the erythritol powder according to the invention, which has a mean grain size of about 12 μm.

The tests were therefore carried out with a commercially available powder-jet device (AirFlow S1™, EMS Electro Medical Systems SA, Switzerland). In the present tests, the plastic material PEEK G 30 was taken as a substitute for the sensitive part of a tooth surface, i.e. a polyetheretherketone with a glass fibre fraction of 30%. The nozzle of the powder-jet device was arranged at a distance of about 2 mm above the plastic material surface, and the powder stream (jet) was activated for about 10 seconds, respectively. The depth of the area which was treated with the respective powder was measured and evaluated as indicator for the abrasion behaviour or the abrasiveness. For comparison, a glycine-based powder of different mean grain sizes was also used.

TABLE 1

Abrasiveness of different powders

| | mean grain size | | |
|---|---|---|---|
| | Ø 65 μm | Ø 20 μm | Ø 12 μm |
| Sodium bicarbonate | 10 | 6 | 3 |
| glycine | 6 | 3 | — |
| mannitol | 12 | 4$^{(*)}$ | — |

TABLE 1-continued

Abrasiveness of different powders

|  | mean grain size | | |
| --- | --- | --- | --- |
|  | Ø 65 μm | Ø 20 μm | Ø 12 μm |
| erythritol | 14 | 6 | 2 |
| mannitol (30%)/ erythritol (70%) |  |  | 3 |

(*)with particle sizes of 23 μm
A value of 10 correspond to the properties of sodium bicarbonate at Ø 65 μm "—" means that the powder could not be delivered with the conventional device

TABLE 2

Miscibility of different powders

|  | mean grain size | | |
| --- | --- | --- | --- |
|  | Ø 65 μm | Ø 20 μm | Ø 12 μm |
| Sodium bicarbonate | 10 | 10 | 5 |
| glycine | 10 | 9 | — |
| mannitol | 10 | 10(*) | — |
| erythritol | 10 | 10 | 8 |
| mannitol (30%)/ erythritol (70%) |  |  | 9 |

(*)with particle sizes of about 23 μm
A value of 10 correspond to the properties of sodium bicarbonate at Ø 65 μm "—" means that the powder could not be delivered with the conventional device The enclosed tables 1 and 2 show the abrasiveness and miscibility of the tested powders vis-à-vis conventional powders of sodium bicarbonate and glycine, respectively, with a mean grain size of about 65 μm. The value 10 corresponds to the respective properties of sodium bicarbonate. From table 1, it can be taken that the abrasiveness of powder consisting of mannitol with a mean grain size of 23 μm is lower than the abrasiveness of sodium bicarbonate, although the miscibility according to table 2 does not worsen. Still smaller particle sizes of, for example, 12 μm can be processed in the use of erythritol in customary powder jet devices, wherein this results in a lower abrasiveness and the miscibility being better than that of conventional sodium bicarbonate.

Particularly amazing is the abrasiveness or miscibility of a powder mixture with a mass fraction of 30% mannitol with mean grain sizes of approx. 23 μm and a mass fraction of 70% erythritol with mean grain sizes of approx. 12 μm (i.e. the amount-of-substance ratio of approx. 1:6, i.e. the ratio of the number of particles has a value of about 1:6 (mannitol: erythritol)), which almost corresponds to the abrasiveness or miscibility of glycine, although the powder mixture has considerable advantages over glycine. Hence, this powder mixture has a lesser corrosion effect on steel and causes lesser wear of the jet nozzle than glycine. Furthermore, the powder mixture is not too toxic and may not—as glycine—cause skin irritation upon contact. The mixture can be manufactured directly and need not—as glycine—be ground and sieved, resulting in a considerable reduction of manufacturing costs. The powder mixture is not cariogenic and can be used with diabetics.

Particularly preferred is the powder described herein, because its cleaning efficiency is considerably better than with conventional powders, i.e. the abrasion of dental plaque takes place faster, presumably because of the crystal morphology of erythritol. In this connection, the following tests were made:

In order to determine the value of the cleaning efficiency of the aforesaid comparative powders and the powder according to the invention, from a coated plate, an area of 1 cm×0.5 cm was respectively treated with the powder coming out of a powder-jet device until said area was completely freed from its coating. The required time was measured. Each test was repeated ten times to take into account statistical variations. The tests were again carried out with a commercially available powder-jet device (AirFlow S1™, EMS Electro Medical Systems SA, Switzerland).

The cleaning efficiency of sodium bicarbonate powder with a particle diameter of 65 μm has, as in the other tests before, been allocated the value 10 for better comparability. The determined times for the other powders have been standardized with this value, and the reciprocal values have been inserted into table 3. Hence, a high point value stands for a good cleaning efficiency.

TABLE 3

Cleaning efficiency of various powders

|  | Ø 65 μm | Ø 20 μm | Ø 12 μm |
| --- | --- | --- | --- |
| sodium bicarbonate | 10 | 11 | 10 |
| glycine | 8 | 8 | — |
| mannitol | 13 | 6 | — |
| erythritol | 21 | 19 | 12 |
| mannitol (30%)/ erythritol (70%) | — |  | 10 |

A value of 10 correspond to the properties of sodium bicarbonate at Ø 65 μm "—" means that the powder could not be delivered with the conventional device The cleaning efficiency of the tested powders is, for almost all sorts of powder, in comparison to the standard powder (sodium bicarbonate with mean grain sizes of about 65 μm), surprisingly either better or at least similar. Only mannitol with a grain size of 20 μm drops off somewhat. The tested glycine powders, too, do not reach the performance of the standard powder. The powders containing erythritol, however, show an excellent cleaning efficiency which was always beyond the one of the standard powder. The cleaning efficiency of the mixture of mannitol and erythritol was also equivalent to the one of the standard powder.

Taking into consideration the determined values for abrasiveness, miscibility and cleaning efficiency, the sorts of powder erythritol 12 μm and the mixture consisting of erythritol and mannitol are superior over the known powders for sensitive dental surfaces. If an abrasion value of 3 is set as upper limit for sensitive dental surfaces, the aforementioned powders meet this value or are even fall below this value. At the same time, they show a better cleaning result than known powders made of glycine.

Although embodiments have been described herein, many other variations and modifications and other uses will become apparent to those skilled in the art. Therefore, the present invention is not limited by the specific disclosure herein.

What is claimed is:
1. A tooth cleaning method, comprising the steps of:
preparing at least one powder containing erythritol as an agent for abrading tooth surfaces;
providing a powder-jet device having a powder chamber and a nozzle;
disposing the powder in the powder chamber;
blowing air into the powder chamber so as to disperse the powder to form a powder/air mixture;
feeding the powder/air mixture to the nozzle, and thereby powder blasting a tooth surface to be cleaned with said powder from the nozzle for a powder jet cleaning of the tooth surface.

2. The method of claim 1, further comprising the step of mixing said powder together with at least one finely particled component selected from the group consisting of silica gel, bleaching agents, analgesics, bacteriocides and flavor additives, for the preparation of said agent.

3. The method of claim 1, wherein the at least one powder consists essentially of two powders, said two powders being a mannitol and an erythritol.

4. The method of claim 3, characterized in that the mannitol is present in a mass fraction of 30% and the erythritol is present in a mass fraction of 70%.

5. The method of claim 3, further comprising the step of mixing said powder together with at least one finely particled component selected from the group consisting of silica gel, bleaching agents, analgesics, bacteriocides and flavor additives, for the preparation of said agent.

6. The method of claim 1, wherein the agent additionally contains water; and comprising the step of blasting said powder/air mixture together with said water onto said tooth surface.

7. The method of claim 1, wherein said powder further comprises a mannitol.

8. The method of claim 1, wherein a mean grain size of the powder is no larger than 35 microns.

9. The method of claim 8, wherein said mean grain size is between 10 and 30 microns.

10. The method of claim 1, wherein said powder consists essentially of erythritol with a mean grain size between 10 and 30 microns.

11. The method of claim 1, characterized in that the powder has a density of no more than 2.0 g/cm$^3$.

12. The method of claim 11, characterized in that the powder has a density of no more than 1.8 g/cm$^3$.

13. The method of claim 12, characterized in that the powder has a density of no more than 1.55 g/cm$^3$.

14. The method of claim 1, characterized in that the powder has Mohs hardness of no more than 4.0.

15. The method of claim 14, characterized in that the powder has Mohs hardness of no more than 3.5.

16. The method of claim 15, characterized in that the powder has Mohs hardness of no more than 2.5.

17. The method of claim 1, characterized in that the powder has a molar mass of no less than 90 g/mol.

18. The method of claim 17, characterized in that the powder has a molar mass of no less than 110 g/mol.

19. The method of claim 18, characterized in that the powder has a molar mass of no less than 120 g/mol.

* * * * *